United States Patent
Kim et al.

(10) Patent No.: US 8,624,201 B2
(45) Date of Patent: Jan. 7, 2014

(54) FLUORESCENCE DETECTING OPTICAL SYSTEM AND MULTI-CHANNEL FLUORESCENCE DETECTION APPARATUS HAVING THE SAME

(75) Inventors: Kyung-ho Kim, Seoul (KR); Joon-ho Kim, Seongnam-si (KR); Kak Namkoong, Seoul (KR); Won-seok Chung, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 112 days.

(21) Appl. No.: 13/421,119

(22) Filed: Mar. 15, 2012

(65) Prior Publication Data

US 2012/0305801 A1    Dec. 6, 2012

(30) Foreign Application Priority Data

May 31, 2011   (KR) ........................ 10-2011-0052400

(51) Int. Cl.
*G01N 21/64* (2006.01)
(52) U.S. Cl.
USPC ...................................... 250/458.1
(58) Field of Classification Search
USPC .......................................... 250/458.1, 459.1
See application file for complete search history.

(56) References Cited

U.S. PATENT DOCUMENTS

| | | | |
|---|---|---|---|
| 5,943,129 A * | 8/1999 | Hoyt et al. | 356/318 |
| 2002/0192808 A1 | 12/2002 | Gambini et al. | |
| 2003/0179469 A1* | 9/2003 | Maeda et al. | 359/719 |
| 2003/0219754 A1 | 11/2003 | Oleksy et al. | |
| 2005/0072899 A1* | 4/2005 | Anzai | 250/201.5 |
| 2005/0179898 A1* | 8/2005 | Mishima | 356/401 |
| 2006/0166355 A1 | 7/2006 | Gutekunst | |
| 2009/0141272 A1 | 6/2009 | Oldham et al. | |
| 2010/0085570 A1* | 4/2010 | Park et al. | 356/364 |
| 2011/0272596 A1* | 11/2011 | Haga et al. | 250/458.1 |
| 2012/0307250 A1* | 12/2012 | Wang et al. | 356/450 |

FOREIGN PATENT DOCUMENTS

| | | |
|---|---|---|
| KR | 10-2007-0064558 A | 1/2009 |
| KR | 10-2009-0053677 A | 12/2009 |

* cited by examiner

*Primary Examiner* — Kiho Kim
(74) *Attorney, Agent, or Firm* — Leydig, Voit & Mayer, Ltd.

(57) ABSTRACT

A fluorescence detecting optical system, and a multi-channel fluorescence detection apparatus comprising same, comprising a light source that emits excitation light, a polarizer that transmits light having a predetermined polarization component, a polarizing beam splitter that transmits light having a predetermined polarization component and reflects light having a different polarization component than the predetermined polarization component, and a quarter-wave plate converting linearly polarized to circularly polarized light or vice versa.

26 Claims, 10 Drawing Sheets

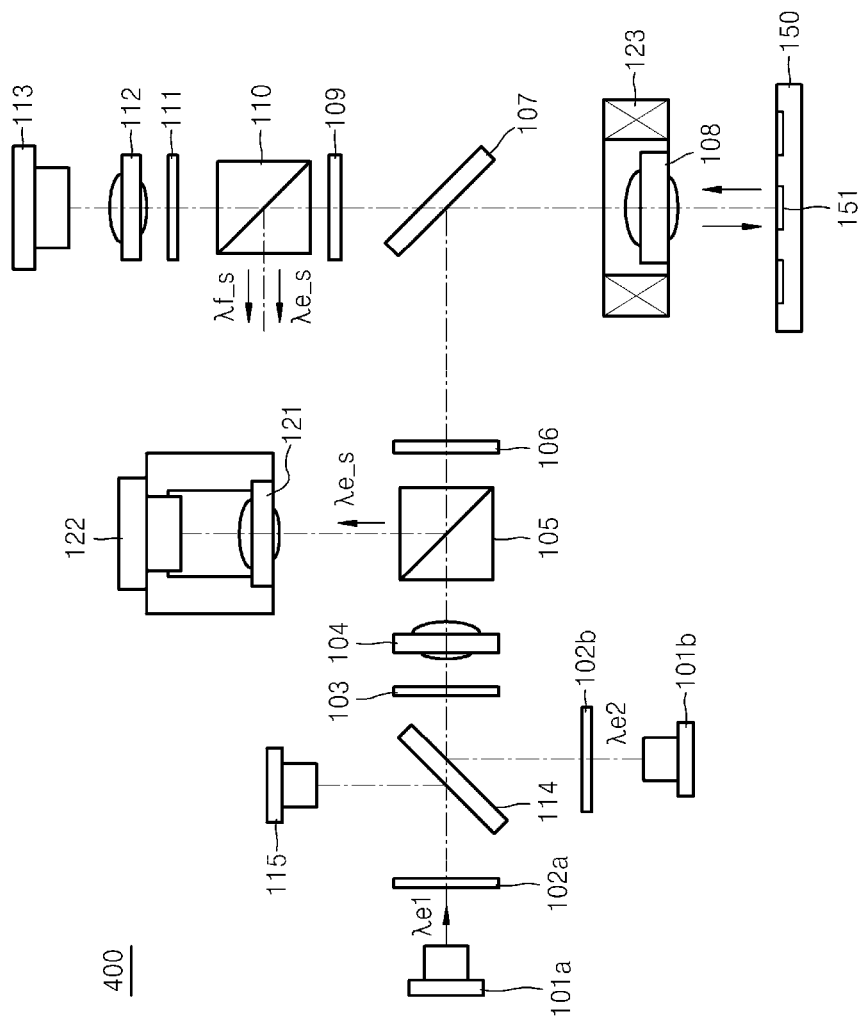

FLUORESCENCE DETECTING OPTICAL SYSTEM AND MULTI-CHANNEL FLUORESCENCE DETECTION APPARATUS HAVING THE SAME

CROSS-REFERENCE TO RELATED APPLICATIONS

This application claims the benefit of Korean Patent Application No. 10-2011-0052400, filed on May 31, 2011, in the Korean Intellectual Property Office, the disclosure of which is incorporated herein in its entirety by reference.

BACKGROUND

With advent of point-of-care (POS) measurements, the importance of, and demand for, gene analysis, in vitro diagnosis (IVD), and gene base sequence analysis continue to increase. To meet the growing importance and demand, platforms and systems have been developed to perform a large number of tests with a small amount of samples. For example, microfluidic platforms and systems for microfluidic chips or lab-on-a-chip applications are receiving considerable attention for high throughout analysis. A microfluidic device includes a plurality of microfluidic channels and chambers designed to control and manipulate a very small amount of fluid. Using a microfluidic device may minimize the reaction time of microfluid and allow simultaneously the reaction of microfluid and measurement of the reaction result. Such a microfluidic device may be fabricated using various methods in which diverse materials are used.

Meanwhile, for example, during gene analysis, in order to precisely detect the presence of specific DNA or the amount of the DNA in a sample, an actual sample has to be sufficiently amplified for measurement after its purification/extraction. Among various gene amplification techniques, polymerase chain reaction (PCR) amplification is most widely used. A fluorescence detection method is commonly used to detect DNA amplified through PCR. For example, quantitative real-time PCR (qPCR) uses a plurality of fluorescent dyes/probes and primer sets to amplify and detect/measure a target sample in real time. The principle of qPCR using a TaqMan probe is that a TaqMan probe falls off a template during DNA amplification, thereby having fluorescent characteristics. That is, as a PCR cycle progresses, the number of TaqMan probes cleaved from each template exponentially increases. As a result, the level of a fluorescence signal exponentially increases. By measuring a change in such a fluorescence signal level with an optical system, the presence of a target sample may be determined and a quantitative analysis of the target sample may be allowed. As a PCR cycle progresses, a fluorescence signal level follows an S-curve in which a threshold cycle Ct is set and measured at the point where the fluorescence signal level rapidly changes. Platforms for IVD, gene analysis, biomarker development, gene base sequence analysis using a qPCR technique have already been commercially available.

A fluorescence detecting optical system is configured to measure the level of a fluorescence signal or a change in the level thereof due to bio reactions within a microfluidic device such as a microfluidic chip or PCR chip. For example, a fluorescence detecting optical system may irradiate excitation light on a sample labeled with a fluorescent dye and detect fluorescence radiated from the fluorescent dye excited with the excitation light. However, most fluorescent dyes have a wavelength region overlapping between wavelength bands of excitation light and fluorescent light. Thus, an excitation light filter and a fluorescent light filter may be designed in such a way that a wavelength band passed by the excitation light filter does not overlap a wavelength band passed by the fluorescent light filter. If the wavelength bands passed by the excitation light filter and the fluorescent light filter overlap each other, the excitation light is not completely separated from the fluorescent light, thereby causing the excitation light reflected from the microfluidic device to be incident on a photodetector. Because excitation light is usually about $10^5$ to $10^6$ times brighter than fluorescent light emitted by a fluorescent dye, crosstalk between the excitation light and the fluorescent light may degrade the detection performance of a fluorescence detecting optical system.

A multi-channel fluorescence detection apparatus including a plurality of fluorescence detecting optical systems for detecting different colors of fluorescence may suffer from crosstalk between excitation light in adjacent wavelength ranges and between fluorescent light in adjacent wavelength ranges according to the design of an excitation light filter, a fluorescent light filter, and a dichroic filter because there is an overlapping region between excitation light in adjacent wavelength ranges and between fluorescent light in adjacent wavelength ranges.

In order to prevent occurrence of such crosstalk, the excitation light filter and the fluorescent light filter are usually designed to pass a narrow wavelength band (several tends of nm). However, as wavelength ranges transmitted by the excitation light filter and the fluorescent light filter decrease, the intensities of the excitation light and the fluorescent light decreases, thereby resulting in the degradation of detection performance. Furthermore, it is difficult to design a plurality of excitation light filters and a plurality of fluorescent light filters so that transmission wavelength bands thereof do not overlap each other. In order to overcome the drawbacks, compensation of crosstalk using software has been proposed. However, this approach is difficult to apply because the result may vary greatly depending on a selected coefficient value.

Furthermore, a portion of excitation light emitted by a light source in a fluorescence detecting optical system is reflected back from a microfluidic device to the light source. This may cause an interference between excitation light emitted by the light source and that reflected from the microfluidic device. The interference between the excitation light may result in noise, thereby adversely affecting the detection performance of the fluorescence detecting optical system.

SUMMARY OF THE INVENTION

Provided are a fluorescence detecting optical system and a multi-channel fluorescence detection apparatus including the same, which may effectively reduce crosstalk between excitation light and fluorescent light or between fluorescent light in adjacent wavelength bands and alleviate noise produced due to reflected excitation light.

Additional aspects will be set forth in part in the description which follows and, in part, will be apparent from the description, or may be learned by practice of the presented embodiments.

According to an aspect of the present invention, a fluorescence detecting optical system includes: a light source unit that emits excitation light having a first polarization component; an objective lens positioned to focus the excitation light onto a microfluidic device (e.g., comprising a fluorescently labeled sample) or other type of fluorescent sample; a fluorescence detector for detecting fluorescent light generated when a sample within the microfluidic device is excited with the excitation light; and a light delivery unit that delivers the excitation light emitted by the light source unit to the microfluidic device or other sample, and delivers the fluorescent light generated in the microfluidic device or by the sample to the fluorescence detector.

The light delivery unit may be configured to convert excitation light reflected from the microfluidic device or other sample to excitation light having a second polarization component perpendicular to the first polarization component and reflect the excitation light having the second polarization component away from an optical path.

The light delivery unit may include: a first beam splitter disposed between the objective lens and the fluorescence detector so as to transmit at least a portion of incident light and reflect the remaining portion thereof; a second beam splitter disposed between the first beam splitter and the light source unit so as to transmit light with the first polarization component and reflects light with the second polarization component; a first quarter-wave plate disposed between the second and first beam splitters; a third beam splitter disposed between the first beam splitter and the fluorescence detector so as to transmit light with the first polarization component and reflect light with the second polarization component; and a second quarter-wave plate disposed between the third beam splitter and the first beam splitter.

For example, the first beam splitter may be a half mirror transmitting 50% of incident light and reflecting the remaining 50% thereof, or a dichroic filter reflecting excitation light and transmitting fluorescent light.

For example, the second and third beam splitters may be polarizing beam splitters.

The fluorescence detecting optical system may further include an automatic focusing unit detecting excitation light having the second polarization component reflected by the second or third beam splitter, calculating a focus error of the objective lens, and adjusting a focus position of the objective lens.

The light source unit may include: a light source emitting excitation light; a polarizer transmitting light having the first polarization component and blocking light having the second polarization component perpendicular to the first polarization component; and a collimating lens collimating the excitation light into a parallel beam.

The light source unit may further include an excitation light filter transmitting only excitation light in a predetermined wavelength band.

The fluorescence detector may include a photodetector detecting fluorescent light emitted from a sample (e.g., within the microfluidic device) and a focusing lens focusing the fluorescent light on the photodetector.

The fluorescence detector may further include a fluorescent light filter transmitting only fluorescent light.

The light source unit may include a light source emitting excitation light and a first band pass filter transmitting only excitation light in a predetermined wavelength band. The fluorescence detector may include a photodetector detecting fluorescent light and a second band pass filter transmitting only fluorescent light. Transmission bands of the first and second band pass filters may partially overlap each other.

In another embodiment, the fluorescence detecting optical system includes: a light source unit that emits two excitation light beams having a first polarization component and different wavelengths; an objective lens positioned to focus excitation light onto a sample (e.g., within a microfluidic device); a fluorescence detector for detecting fluorescent light generated when a sample (e.g., within the microfluidic device) is excited with the excitation light; and a light delivery unit that delivers the excitation light emitted by the light source unit to the sample (e.g. within a microfluidic device) and deliver the fluorescent light generated by the sample (e.g., in the microfluidic device) to the fluorescence detector. The light delivery unit may be configured to convert excitation light reflected from the sample or microfluidic device to excitation light having a second polarization component perpendicular to the first polarization component and reflect the excitation light having the second polarization component away from an optical path.

The light delivery unit may include: a first beam splitter disposed between the objective lens and the fluorescence detector so as to transmit at least a portion of incident light and reflect the remaining portion thereof; a second beam splitter disposed between the first beam splitter and the light source unit so as to transmit light with the first polarization component and reflect light with the second polarization component; a first quarter-wave plate disposed between the second and first beam splitters; a third beam splitter disposed between the first beam splitter and the fluorescence detector so as to transmit light with the first polarization component and reflect light with the second polarization component; and a second quarter-wave plate disposed between the third beam splitter and the first beam splitter.

The fluorescence detecting optical system may further include an automatic focusing unit detecting excitation light having the second polarization component reflected by the second or third beam splitter, calculating a focus error of the objective lens, and adjusting a focus position of the objective lens.

The automatic focusing unit may include: a divided-type photodetector with a plurality of photo-detecting segments; a focusing lens focusing excitation light onto the divided-type photodetector; and an actuator adjusting a focus position of the objective lens.

For example, the focusing lens may be an astigmatic lens and the segment type photodetector may be a quad type photodetector having four photo-detecting segments.

The automatic focusing unit may further include a knife-edge disposed between the focusing lens and the divided-type photodetector so as to block off unfocused light. The segment type photodetector may be a dual type photodetector having two photo-detecting segments.

The light source unit may include: a first light source emitting first excitation light; a first excitation light filter passing the first excitation light; a second light source emitting second excitation light having a different wavelength than the first excitation light; a second excitation light filter passing the second excitation light; a beam splitter that is disposed opposite the first and second light sources and reflects or transmits the first and second excitation light so that the first and second excitation light propagate along the same optical path; a polarizer transmitting light having the first polarization component and blocking light having the second polarization component perpendicular to the first polarization component; and a collimating lens collimating excitation light into a parallel beam.

For example, each of the first and second excitation light filters may be the same dual band pass filter that transmits both of the first and second excitation light.

For example, the beam splitter may be a half mirror designed to transmit more than about 95% of light incident on a first surface thereof opposite to the first light source while reflecting more than 95% of light incident on a second surface opposite to the second light source.

The light source unit may further include a monitoring photodetector measuring the intensities of first excitation light reflected by the beam splitter and the second excitation light transmitted by the beam splitter.

The fluorescence detector may include a photodetector detecting fluorescent light emitted from a sample (e.g., within the microfluidic device) and a focusing lens focusing the fluorescent light on the photodetector.

For example, the fluorescent light filter may be a dual band pass filter that passes both of two fluorescent light beams having different wavelengths generated when the sample (e.g., within the microfluidic device) is excited with two excitation light beams having different wavelengths.

According to another aspect of the present invention, a fluorescence detection apparatus includes at least one fluorescence detecting optical system having the above-described construction and a transport element transporting the at least one fluorescence detecting optical system.

BRIEF DESCRIPTION OF THE DRAWINGS

These and/or other aspects will become apparent and more readily appreciated from the following description of the embodiments, taken in conjunction with the accompanying drawings of which:

FIG. 6 schematically illustrates an exemplary construction of a fluorescence detecting optical system according to another embodiment of the present invention;

DETAILED DESCRIPTION

Figure 1:
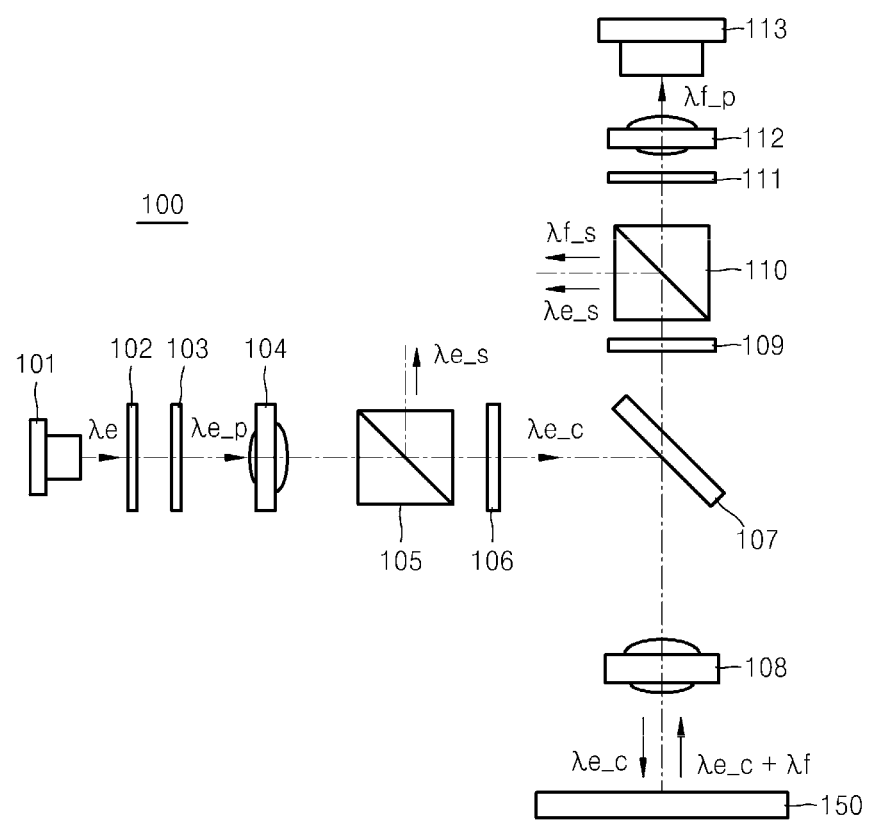
FIG. 1 schematically illustrates an exemplary construction of a fluorescence detecting optical system according to an embodiment of the present invention.

Reference will now be made in detail to embodiments, examples of which are illustrated in the accompanying drawings, wherein like reference numerals refer to the like elements throughout. In the drawings, the size of each element may be exaggerated for clarity and convenience of explanation. In this regard, the present embodiments may have different forms and should not be construed as being limited to the descriptions set forth herein. Accordingly, the embodiments are merely described below, by referring to the figures, to explain aspects of the present description.

FIG. 1 schematically illustrates an exemplary construction of a fluorescence detecting optical system 100 according to an embodiment of the present invention. Referring to FIG. 1, the fluorescence detecting optical system 100 according to the present embodiment includes a light source 101 emitting excitation light, a beam splitter 107 reflecting a portion of incident light and transmitting the remaining portion thereof, an objective lens 108 focusing the excitation light reflected by the beam splitter 107 onto a chamber (FIG. 2 at 151) of a microfluidic device 150, and a photodetector 113 detecting fluorescent light generated in a sample within the chamber 151. The fluorescence detecting optical system 100 further includes an excitation light filter 102, a polarizer 103, a collimating lens 104, a first polarizing beam splitter 105, and a first quarter-wave plate 106 located in an optical path between the light source 101 and the beam splitter 107. The excitation light filter 102 transmits only excitation light having a predetermined wavelength range. The polarizer 103 transmits light having a first polarization component and blocks light having a second polarization component perpendicular to the first polarization component. The collimating lens 104 collimates the excitation light into a parallel beam. The first polarizing beam splitter 105 transmits light having the first polarization component and reflects light having the second polarization component perpendicular thereto. The first quarter-wave plate 106 delays the phase of incident light by one quarter of a wavelength of the incident light. The fluorescence detecting optical system 100 further includes a second quarter-wave plate 109, a second polarizing beam splitter 110, a fluorescent light filter 111, and a focusing lens 112 located in an optical path between the beam splitter 107 and the photodetector 113. The second quarter-wave plate 109 retards the phase of incident light by a quarter of a wavelength of the incident light, a second polarizing beam splitter 110 transmits light having the first polarization component and reflects light having the second polarization component perpendicular thereto. The fluorescent light filter 111 transmits only fluorescent light of the light transmitted through the second polarizing beam splitter 110. The focusing lens 112 focuses fluorescent light onto the photodetector 113.

In the above construction, the light source 101, the excitation light filter 102, the polarizer 103, and the collimating lens 104 form a light source unit. For example, the light source 101 may be a laser diode (LD) or light-emitting diode (LED) emitting light of a predetermined wavelength, or a halogen lamp or white LED emitting white light. The excitation light filter 102 may be a band pass filter that transmits only excitation light λe in a predetermined wavelength band. For example, the excitation light filter 102 may be designed to transmit excitation light in a wavelength band having the highest absorption rate with respect to a fluorescent dye used to label a sample within the chamber 151. Although FIG. 1 shows the excitation light filter 102 is disposed immediately in front of the light source 101, it is not limited thereto. For example, the excitation light filter 102 may be disposed anywhere between the light source 101 and the beam splitter 107.

The polarizer 103 transmits excitation light with the first polarization component (e.g., p-polarization) and blocks excitation light with the second polarization component (e.g., s-polarization) perpendicular thereto. Thus, the excitation light that has passed through the polarizer 103 has only the first polarization component. Although FIG. 1 shows the polarizer 103 is disposed between the excitation light filter 102 and the collimating lens 104, it is not limited thereto. For example, the polarizer 103 may be disposed anywhere between the light source 101 and the first polarizing beam splitter 105. Furthermore, when the light source 101 emits unpolarized light, the polarizer 103 is used. Thus, when the light source 101 is a polarized light source that emits light with a predetermined polarization component, the polarizer 103 may be omitted.

The fluorescent light filter 111, the focusing lens 112, and the photodetector 113 form a fluorescence detecting unit that detects fluorescent light generated in the chamber 151 of the microfluidic device 150. The fluorescent light filter 111 blocks other light than fluorescent light so as not to reach the photodetector 113. For example, the fluorescent light filter 111 may be a band pass filter that passes only fluorescent light λf in a second wavelength band generated when a sample within the chamber 151 is excited with excitation light in a first wavelength band. For example, the photodetector 113 may be a photodiode (PD), a photodiode array, a photo multiplier tube (PMT), a charge-coupled device (CCD) image sensor, a complementary metal-oxide semiconductor (CMOS) image sensor, or an avalanche PD (APD).

Meanwhile, the first polarizing beam splitter 105, the first quarter-wave plate 106, the beam splitter 107, the second quarter-wave plate 109, and the second polarizing beam splitter 110 form a light delivery unit that delivers excitation light emitted by the light source 101 to the microfluidic device 150 and fluorescent light generated in the chamber 151 of the microfluidic device 150 to the photodetector 113. The first and second polarizing beam splitter 105 and 110 transmits or reflects incident light according to the polarization direction of the incident light. For example, the first and second polarizing beam splitters 105 and 110 may transmit light of the first polarization component (e.g., p-polarization) and reflects light of the second polarization component (e.g., s-polarization) perpendicular thereto. The first and second quarter-wave plates 106 and 109 delay the phase of incident light by one quarter of a wavelength of the incident light. According to optical principles, a quarter-wavelength phase shift converts linearly polarized light to circularly polarized light and vice versa. When the linearly polarized light passes through the first or second quarter wave-plate 106 or 109 twice, it suffers a half-wavelength phase delay and is changed to linearly polarized light having a polarization direction perpendicular to the original polarization direction. For example, p-polarized light may be converted to s-polarized light as it passes through the first or second quarter-wave plate 106 or 109 twice.

The beam splitter 107 transmits a portion of incident light and reflects the remaining portion thereof. For example, the beam splitter 107 may be a half mirror disposed at 45 degrees with respect to an optical axis. In this case, the half mirror may be designed to transmit 50% of incident light and reflect the remaining 50% thereof. Instead of the half mirror, a dichroic mirror having wavelength selectivity may be used as the beam splitter 107. For example, the dichroic mirror may reflect excitation light λe in the first wavelength band and transmit fluorescent light λf in the second wavelength band. Although FIG. 1 shows an optical path between the light source 101 and the microfluidic device 150 is bent while an optical path between the photodetector 113 and the microfluidic device 150 is straight, it is not limited thereto. Depending on the type of the beam splitter 107 used, the optical path between the light source 101 and the microfluidic device 150 may be straight while the optical path between the photodetector 113 and the microfluidic device 150 may be bent. To achieve this, if the beam splitter 107 is a half mirror, it may rotate by 90 degrees. Alternatively, the beam splitter 107 may be a dichroic filter that transmits excitation light λe in the first wavelength band and reflects fluorescent light λf in the second wavelength band.

Hereinafter, the operation of the fluorescence detecting optical system 100 is described in detail with reference to FIG. 1. For convenience of explanation, it is assumed that the polarizer 103 transmits light having p-polarization component while blocking light having s-polarization component. The first and second beam splitters 105 and 110 are assumed to transmit light having p-polarization component and reflect light having s-polarization component. The beam splitter 107 is assumed to be a half mirror inclined at 45 degrees with respect to an optical axis.

First, the light source 101 emits excitation light upon being turned on. The excitation light has only a first wavelength band as it passes through the excitation light filter 102. Thereafter, the excitation light becomes polarized to have a predetermined polarization component (e.g., p-polarization) as it passes through the polarizer 103. The resulting excitation light is collimated into a parallel beam by the collimating lens 104. The excitation light λe_p having the p-polarization component passes through the first polarizing beam splitter 105 and is converted to excitation light λe_c having circular polarization by the first quarter-wave plate 106. A portion of the excitation light λe_c is then reflected by the beam splitter 107 and focused onto the chamber 151 of the microfluidic device 150 by the objective lens 108.

The fluorescent dye used to label the sample within the chamber 151 is excited by the excitation light to emit fluorescent light λf in the second wavelength band. The fluorescent light is unpolarized light having all polarization components. To reflect the excitation light and fluorescent light, the microfluidic device 150 may be formed of a reflective material such as silicon. Alternatively, a reflective coating is formed on the microfluidic device 150. Thus, the remaining portion of the excitation light λe_c not absorbed into the fluorescent dye and the fluorescent light λf emitted by the fluorescent dye are reflected from the microfluidic device 150 onto the beam splitter 107.

Then, portions of the excitation light (λe_c) and fluorescent light λf are transmitted by the beam splitter 107 toward the second quarter-wave plate 109 while the remaining portions thereof are reflected by the beam splitter 107 toward the first quarter-wave plate 106. As the remaining portions pass through the first quarter-wave plate 106, the excitation light λe_c having the circular polarization is converted to excitation light λe_s having s-polarization component. On the other hand, the fluorescent light still remains unpolarized. The excitation light λe_s having the s-polarization component is thereafter reflected by the first polarizing beam splitter 105, thereby deviating from an optical path. Thus, because the excitation light reflected from the microfluidic device 150 is not incident on the light source 101, it is possible to suppress noise due to interference of the excitation light. Meanwhile, fluorescent light having a p-polarization component in the fluorescent light that is incident on the first polarizing beam splitter 105 passes through the first polarizing beam splitter 105 but is blocked by the excitation light filter 102. Furthermore, since the fluorescent light has much lower intensity than the excitation light, it slightly affects the operation of the light source 101.

As the portions of the excitation light λe_c and fluorescent light λf transmitted by the beam splitter 107 passes through the second quarter-wave plate 109, the excitation light λe_c having the circular polarization is changed to excitation light λe_s having an s-polarization component. The fluorescent light still remains unpolarized. The excitation light λe_s having the s-polarization component is thereafter reflected by the second polarizing beam splitter 110, thereby deviating from an optical path. That is, because the excitation light reflected from the microfluidic device 150 does not reach the fluorescent light filter 111, it is possible to reduce the possibility that interference may occur between the excitation light and fluorescent light in the photodetector 113. Meanwhile, fluorescent light having a p-polarization component in the fluorescent light incident on the second polarizing beam splitter 110 passes through the second polarizing beam splitter 110, the fluorescent light filter 111 and the focusing lens 113 and is incident on the photodetector 113.

As described above, the fluorescence detecting optical system 100 uses polarizing elements such as the polarizer 103, the first and second polarizing beam splitters 105 and 110, and the first and second quarter-wave plates 106 and 109 to appropriately control the propagation paths of the excitation light and the fluorescent light. In particular, by reflecting the remaining excitation light reflected from the microfluidic device 150 away from the optical path, the remaining excitation light may be prevented from entering the light source 101 and the photodetector 113. Thus, according to the present embodiment, optical crosstalk may be minimized without using software. It is also possible to suppress noise due to the excitation light reflected from the microfluidic device 150 reentering the light source 101. Even when the light source 101 emitting white light is used, it is not necessary to design a separate filter for blocking infrared (IR) light and ultraviolet (UV) light. Furthermore, by using an affordable half mirror as well as expensive dichroic filter, the manufacturing costs of the fluorescence detecting optical system 100 may be further reduced.

Figure 2:
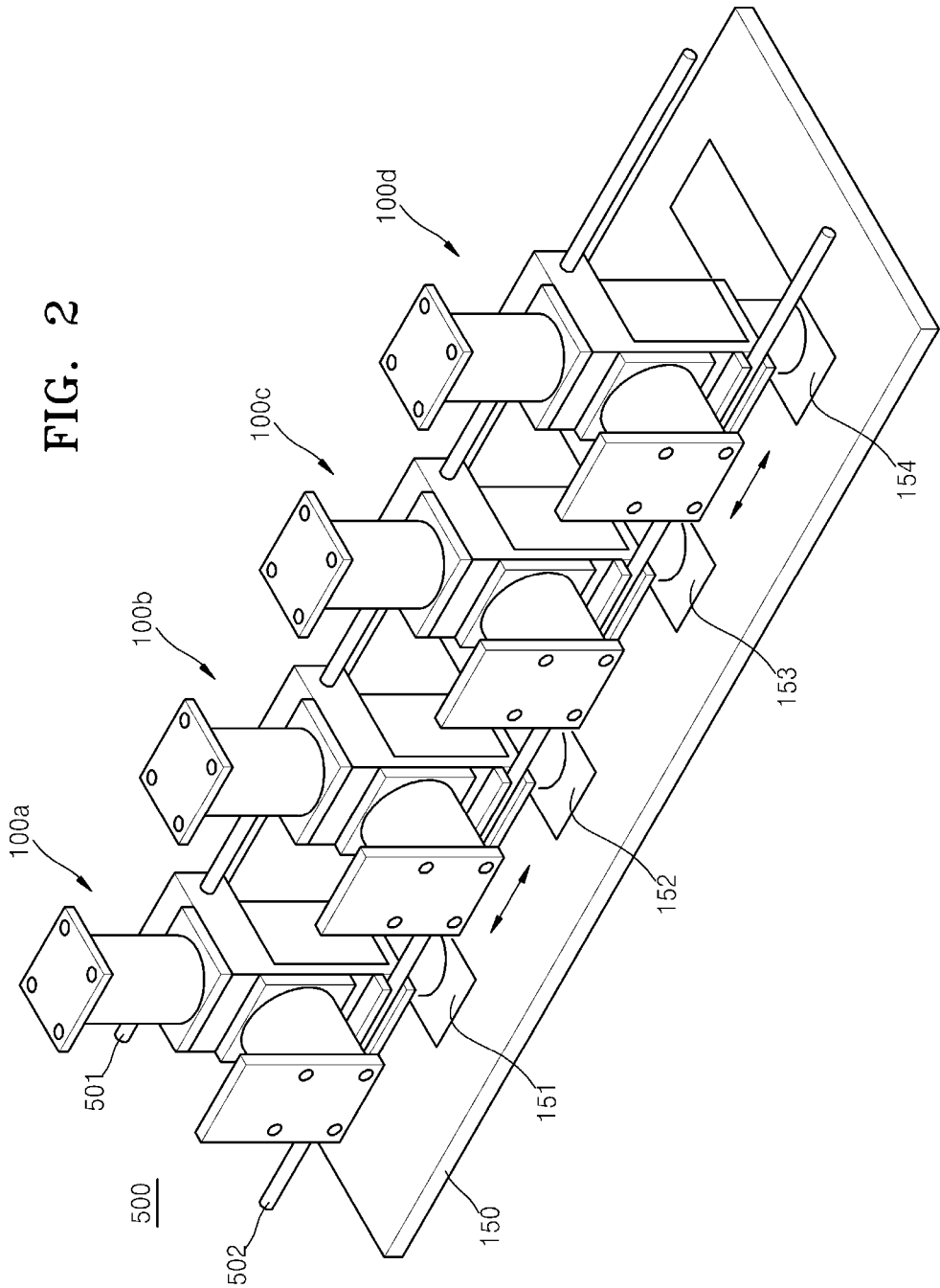
FIG. 2 schematically illustrates an exemplary construction of a multi-channel fluorescence detection apparatus according to an embodiment of the present invention.

By combining a plurality of fluorescence detecting optical systems 100, a multi-channel fluorescence detection apparatus capable of simultaneously detecting fluorescence for multiple colors is achieved. FIG. 2 schematically illustrates an exemplary construction of a multi-channel fluorescence detection apparatus 500 including the above-described fluorescence detecting optical system 100, according to an embodiment of the present invention. Referring to FIG. 2, the multi-channel fluorescence detection apparatus 500 includes first through fourth fluorescence detecting optical systems 100a through 100d detecting fluorescent light in different wavelength bands using excitation light in different wavelength bands. Although the multi-channel fluorescence detection apparatus 500 includes the four fluorescence detecting optical systems 100a through 100d, it is not limited thereto. Each of the four fluorescence detecting optical systems 100a through 100d has the same construction as illustrated in FIG. 1, except for wavelengths of excitation light and fluorescent light.

For example, the first and second fluorescence detecting optical systems 100a and 100b may be constructed to irradiate excitation light in first and third wavelength bands and detect fluorescent light in second and fourth wavelength bands, respectively. The third and fourth fluorescence detecting optical systems 100c and 100d may be constructed to irradiate excitation light in fifth and seventh wavelength bands and detect fluorescent light in sixth and eighth wavelength bands, respectively.

To achieve this, each of the first through fourth fluorescence detecting optical systems 100a through 100d includes the excitation light filter 102 and the fluorescent light filter 111 having different transmission bands. According to the polarization principles, as described above, each of the first through fourth fluorescence detecting optical systems 100a through 100d prevents the remaining excitation light from entering the light source 101 and the photodetector 113. Thus, the excitation light filter 102 and the fluorescent light filter 111 in each of the first through fourth fluorescence detecting optical systems 100a through 100d may be designed without considering crosstalk. That is, multiple excitation light filters 102 and multiple fluorescent light filters 111 do not have to be designed so that the transmission bands do not overlap each other.

Figure 3:
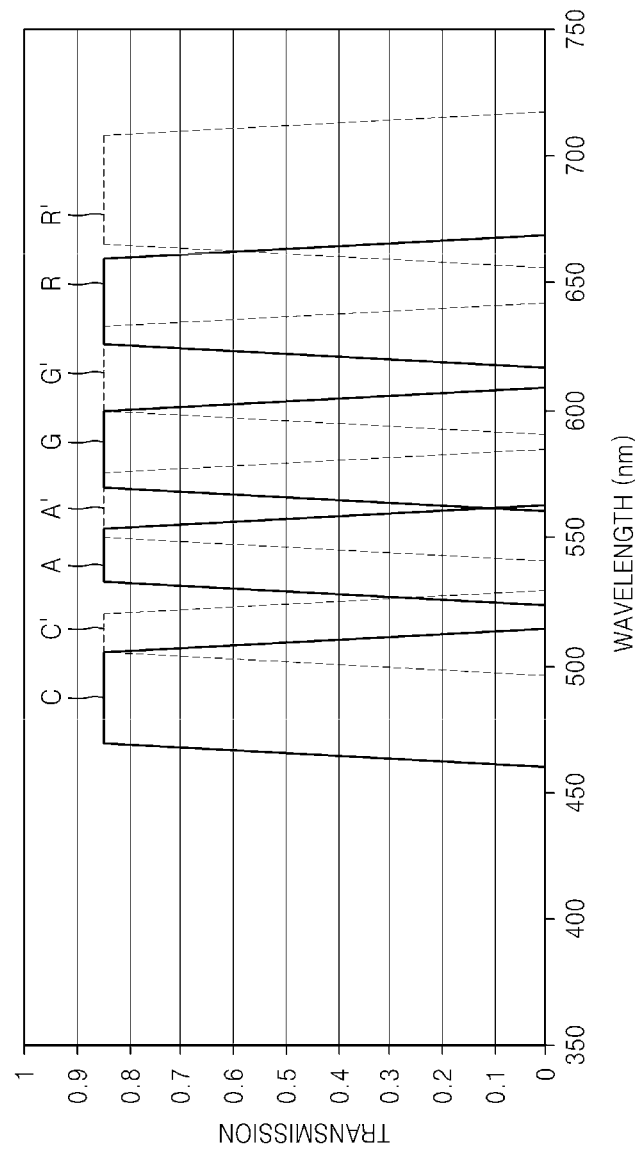
FIG. 3 illustrates transmission bands of a plurality of excitation light filters and a plurality of fluorescent light filters used in the multi-channel fluorescence detection apparatus of FIG. 2.

FIG. 3 illustrates transmission bands of multiple excitation light filters 102 and multiple fluorescent light filters 111 in the respective first through fourth fluorescence detecting optical systems 100a through 100d used in the multi-channel fluorescence detection apparatus 500 of FIG. 2. For example, when the first fluorescence detecting optical system 100a detects fluorescent light using cyan excitation light, transmission bands C and C' of the excitation light filter 102 and the fluorescent light filter 111 may partially overlap each other. In the second fluorescence detecting optical system 100b detecting fluorescent light using amber excitation light, transmission bands A and A' of the excitation light filter 102 and the fluorescent light filter 111 may partially overlap each other. In the third fluorescence detecting optical system 100c detecting fluorescent light using green excitation light, the transmission bands G and G' of the excitation light filter 102 and the fluorescent light filter 111 may partially overlap each other. In the fourth fluorescence detecting optical system 100d detecting fluorescent light using red excitation light, the transmission bands R and R' of the excitation light filter 102 and the fluorescent light filter 111 may partially overlap each other. Furthermore, adjacent channels may partially overlap each other. For example, there may be partial overlaps between transmission bands A' and G and between transmission bands G' and R. Thus, by designing the excitation light filter 102 and the fluorescent light filter 111 so as to have wide transmission bands, the detection performance of the multi-channel fluorescence detection apparatus 500 may be improved. In particular, by designing the excitation light filter 102 and the fluorescent filter 111 to have transmission bands centered at an excitation absorption peak and an emission peak of a fluorescent dye, respectively, light utilization efficiency of the fluorescence detection apparatus 500 may be enhanced.

Referring to FIG. 2, the multi-channel fluorescence detection apparatus 500 according to the present embodiment further includes a lead screw 501 and a guide rail 502 as a transport element for transporting the first through fourth fluorescence detecting optical systems 100a through 100d along a path defined by the rail. Each of the first through fourth fluorescence detecting optical systems 100a through 100d has one end engaged to the lead screw 501 and the other end supported by the guide rail 502. In the above construction, when a motor (not shown) connected to the lead screw 501 rotates the lead screw 501, the fluorescence detecting optical systems 100a through 100d may move along directions indicated by arrows in FIG. 2. The one or more optical systems, for instance, can be transported relative to a surface, sample, or array of samples. Thus, the first through fourth fluorescence detecting optical systems 100a through 100d may detect fluorescence while simultaneously moving over multiple chambers 151 through 154 in a sequential way.

This foregoing exemplary constructions of an apparatus are described with reference to a first through fourth fluorescence detecting optical systems for the purposes of illustration, but are not limited to any particular number of fluorescence detecting optical systems.

Figure 4:
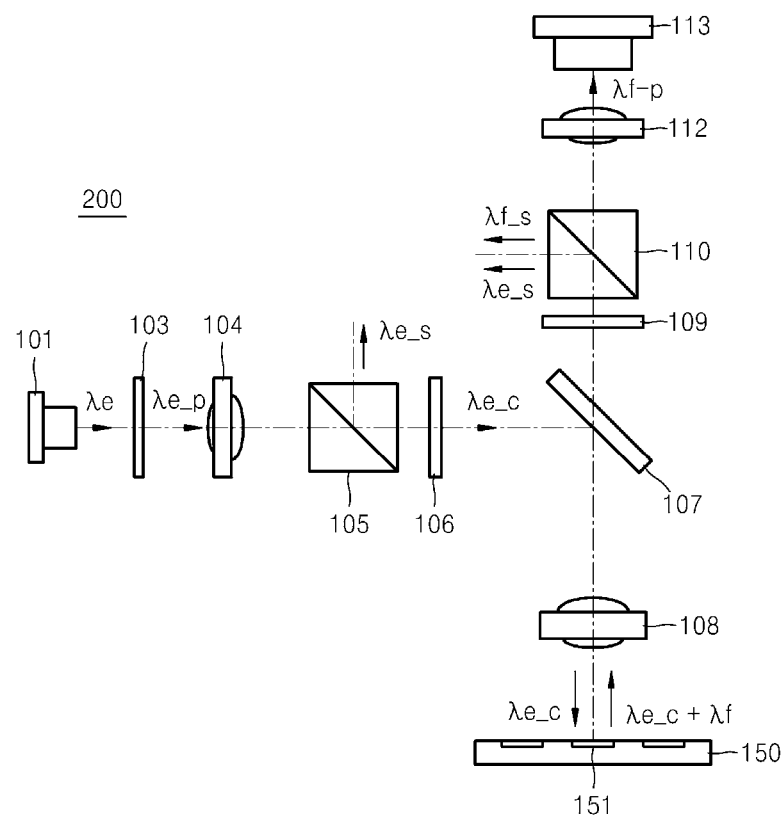
FIG. 4 schematically illustrates an exemplary construction of a fluorescent detecting optical system according to another embodiment of the present invention.

FIG. 4 schematically illustrates an exemplary construction of a fluorescence detecting optical system 200 according to another embodiment of the present invention. The fluorescence detecting optical system 200 has the same construction as the fluorescence detecting optical system 100 except for omission of the excitation light filter 102 and the fluorescent light filter 111. Instead of being used in the multi-channel fluorescence detection apparatus 500, the fluorescence detecting optical system 200 may be separated and used individually for detection of single color fluorescence. Because there is no possibility of interference between adjacent channels when the fluorescence detecting optical system 200 is used individually, the excitation light filter 102 and the fluorescent light filter 111 may be omitted. Despite the absence of the fluorescent light filter 111, the remaining excitation light is not incident on a photodetector 113 because it is deviated from an optical path by a second polarizing beam splitter 110. Furthermore, when excitation wavelengths and fluorescence emission wavelengths of a FAM dye (cyan) and Quasar 670 fluorescent dye (red) are far apart from each other, there may be little possibility of interference therebetween. Thus, in this case, two-color fluorescence detection may be performed simultaneously using two fluorescence detecting optical systems 200.

Figure 5:
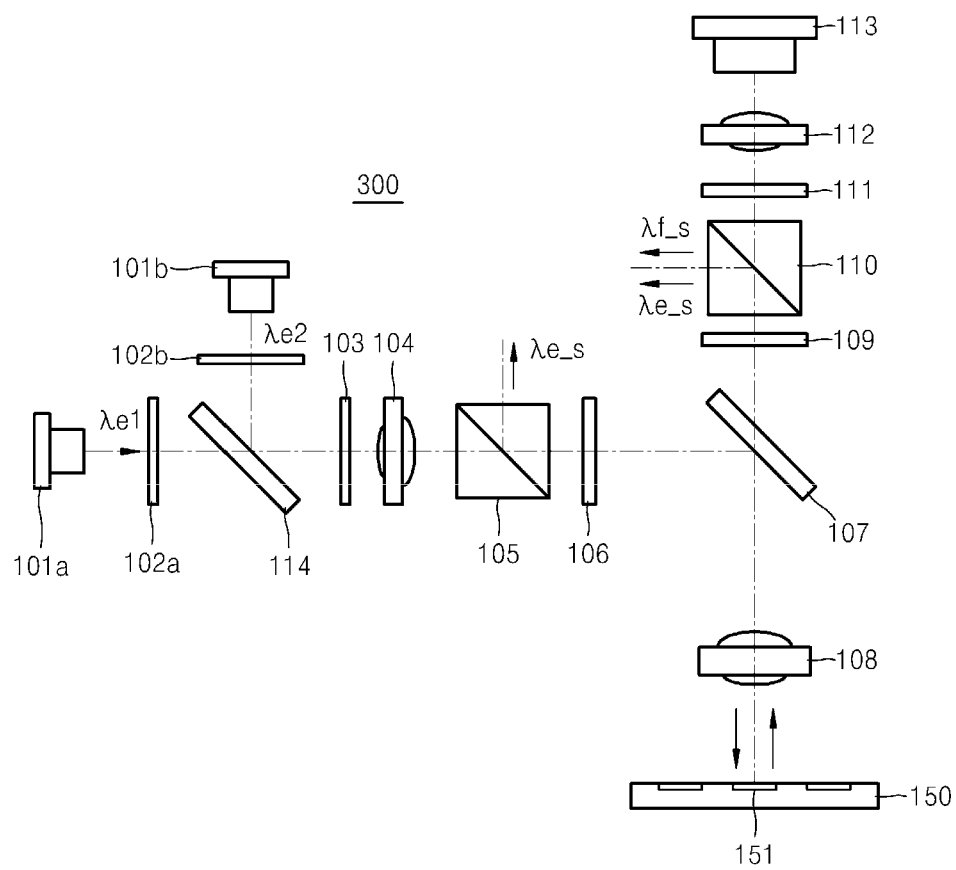
FIG. 5 schematically illustrates an exemplary construction of a fluorescence detecting optical system according to another embodiment of the present invention.

FIG. 5 schematically illustrates an exemplary construction of a fluorescence detecting optical system 300 according to another embodiment of the present invention. The fluorescence detecting optical system 300 according to the present embodiment may be constructed to detect fluorescence with excitation light having two different wavelengths. To achieve this, a light source unit of the fluorescence detecting optical system 300 includes two light sources 101a and 101b, two excitation light filters 102a and 102b, a beam splitter 114, a polarizer 103, and a collimating lens 104. The light source unit uses two different light sources 101a and 101b to provide first and second excitation light $\lambda e1$ and $\lambda e2$ of two different wavelengths. For example, the first and second light sources 101a and 101b may be LEDs or LDs emitting light of different wavelengths. The first and second excitation light filters 102a and 102b may be band pass filters that pass only the first excitation light $\lambda e1$ and the second excitation light $\lambda e2$, respectively. In order to reduce the number of component types and facilitate assembling, the first and second excitation light filters 102a and 102b may be the same filters. For example, the first and second excitation light filters 102a and 102b may be dual band pass filters that transmit both of the first and second excitation light $\lambda e1$ and $\lambda e2$.

The beam splitter 114 causes the first and second excitation light $\lambda e1$ and $\lambda e2$ to propagate along the same optical path. To achieve this, the beam splitter 114 may be inclined at about 45 degrees so as to face the first and second light sources 101a and 101b. For example, the beam splitter 114 may be a half mirror that transmits a portion of incident light and reflects the remaining portion thereof. In this case, a portion of the first excitation light $\lambda e1$ emitted by the first light source 101a is transmitted through the beam splitter 114 to the polarizer 103. A portion of the second excitation light $\lambda e2$ emitted by the second light source 101b is reflected by the beam splitter 114 onto the polarizer 103. For example, the half mirror may be designed to transmit more than about 95% of light incident on one surface thereof opposite to the first light source 101a while reflecting more than 95% of light incident on the other surface opposite to the second light source 101b. Instead of the half mirror, the beam splitter 114 may be a dichroic filter that transmits the first excitation light $\lambda e1$ and reflects the second excitation light $\lambda e2$. In this case, most of the first excitation light $\lambda e1$ emitted by the first light source 101a is transmitted through the beam splitter 114 to the polarizer 103 while most of the second excitation light $\lambda e2$ is reflected by the beam splitter 114 to the polarizer 103.

The rest of the construction and operation of the fluorescence detecting optical system 300 except for the light source unit are almost the same as the structure and operation of the fluorescence detecting optical system 100 of FIG. 1. A fluorescent filter 111 may be a dual band pass filter that transmits both of first fluorescent light emitted from a sample by first excitation light and second fluorescent light emitted from a sample by second excitation light.

In the above-described construction, while the first light source 101a being turned on emits first excitation light, the second light source 101b is turned off and does not emit excitation light. Thus, fluorescence detecting for a sample may be performed with the first excitation light. The operation of detecting fluorescence with the first excitation light is performed in the same manner as the operation of the fluorescence detecting optical system 100 described with reference to FIG. 1. Subsequently, while the second light source 101b being turned on emits second excitation light, the first light source 101a is turned off and does not emit excitation light. Thus, fluorescence detecting for a sample may be performed with the second excitation light. When the multi-channel fluorescence detection apparatus 500 of FIG. 2 includes the fluorescence detecting optical system 300 of FIG. 5, two fluorescence detecting optical systems 300 may be used for four color fluorescence detection.

The foregoing exemplary construction is described above with reference to a first and second light source for the purposes of illustration, but can further comprise additional light sources (e.g., a third, fourth, or fifth light source, etc.). Such additional light sources can be utilized in the same manner, for example, by using additional light sources, excitation light filters, and beam splitters configured in the same manner as depicted in FIG. 5 with respect to the first and second light sources.

FIG. 6 schematically illustrates an exemplary construction of a fluorescence detecting optical system 400 according to another embodiment of the present invention. Unlike the fluorescence detecting optical system 300 of FIG. 5, the fluorescence detecting optical system 400 according to the present embodiment further includes a monitoring photodetector 115 that measures the intensity of excitation light and an automatic focusing unit 121 through 123 that calculates a focus error of the excitation light and adjusts a focus position of an objective lens 108.

For example, the monitoring photodetector 115 may monitor the intensity of first excitation light reflected by a beam splitter 114 and constantly maintain an output of the first light source 101a. The monitoring photodetector 115 may also monitor the intensity of second excitation light transmitted by the beam splitter 114 and constantly maintain an output of the second light source 101b. To achieve this, the beam splitter may be a half mirror that transmits, for example, more than about 95% of light incident on one surface thereof opposite to the first light source 101a (and reflecting less than about 5%) while reflecting, for example, more than 95% of light incident on the other surface opposite to the second light source 101b (and transmitting less than about 5%). While the first light source 101a is turned on, most (e.g., more than about 95%) of the first excitation light is transmitted through the beam splitter 114 and used for detecting fluorescence, and the remaining portion (less than about 5%) is reflected by the beam splitter 114 and used for controlling an optical output of the first light source 101a. Similarly, while the second light source 101b is turned on, most (e.g., more than about 95%) of the second excitation light is transmitted through the beam splitter 114 and used for detecting fluorescence, and the remaining portion (e.g., less than about 5%) is reflected by the beam splitter 114 and used for controlling an optical output of the second light source 101b.

Meanwhile, in the embodiments described with reference to FIGS. 1, 4, and 5, the excitation light $\lambda e\_s$ having an s-polarization component reflected from the microfluidic device 150 is reflected again by the first polarizing beam splitter 105 and is discarded. However, in the embodiment described with reference to FIG. 6, excitation light $\lambda e\_s$ having s-polarization component reflected by the first polarizing beam splitter 105 is used to perform an automatic focusing function. To achieve this, the automatic focusing unit 121 through 123 is disposed opposite a reflecting surface of the first polarizing beam splitter 105. The automatic focusing unit 121 through 123 includes a focusing lens 121 focusing excitation light reflected by the first polarizing beam splitter 105, a divided-type type photodetector 122 detecting the excitation light reflected by the first polarizing beam splitter 105, and an actuator 123 for adjusting a focus position of the objective lens 108. The divided-type photodetector 122 having a plurality of photo-detecting segments measures the intensity of light incident on each of the plurality of photo-detecting segments. Then, an output of the segment type photodetector 122 is used to calculate a focus error of the objective lens 108, and the operation of the actuator 123 is controlled based on the focus error. The automatic focusing unit 121 through 123 may calculate a focus error and adjust a focal point using astigmatism or knife-edge.

Figure 7A:
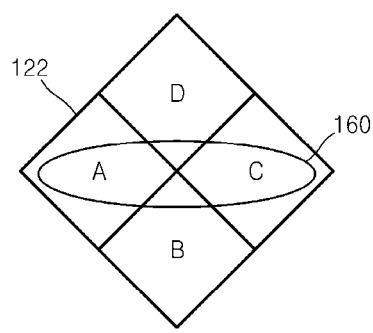
FIGS. 7A through 7C illustrate the principle of adjusting a focal point using astigmatism in the fluorescence detecting optical system of FIG. 6.
Figure 7B:
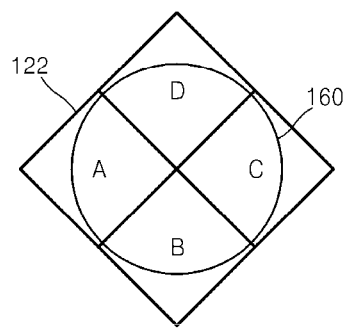
Figure 7C:
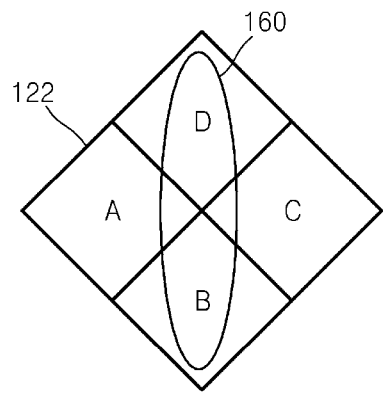

FIGS. 7A through 7C illustrate the principle of adjusting a focal point using astigmatism in the fluorescence detecting optical system 400 of FIG. 6. When the focal point is adjusted using astigmatism, the focusing lens 121 may be an astigmatic lens and the divided-type photodetector 122 may be a quad type photodetector having four segments A through D. When the objective lens 108 comes too close to a chamber 151 of the microfluidic device 150, a light spot 160 formed on the divided-type photodetector 122 by the focusing lens 121 is long in a transverse direction as shown in FIG. 7A. The sum of intensities ("A+C") measured in the first and third segments A and C is greater than the sum of intensities ("B+D") measured in the second and fourth segments B and D. Thus, if A+C>B+D, the actuator 123 operates so that the objective lens 108 moves away from the chamber 151 of the microfluidic device 150. For example, the actuator 123 may be a voice coil motor (VCM).

Conversely, referring to FIG. 7B, when the excitation light is focused precisely on the chamber 151 of the microfluidic device 150, a perfectly circular light spot 160 is formed on the divided-type photodetector 122 by the focusing lens 121. Thus, the sum of light intensities ("A+C") measured in the first and third segments A and C is equal to the sum of light intensities ("B+D") measured in the second and fourth segments B and D. In this case, the position of the objective lens 108 does not need to be adjusted. When the objective lens 108 is too far away from the chamber 151 of the microfluidic device 150, a light spot 160 formed on the divided-type photodetector 122 by the focusing lens 121 is long in a longitudinal direction as shown in FIG. 7C. Thus, the sum of light intensities ("A+C") measured in the first and third segments A and C is less than the sum of light intensities ("B+D") measured in the second and fourth segments B and D. Thus, if A+C<B+D, the actuator 123 operates so that the objective lens 108 moves closer to the chamber 151 of the microfluidic device 150.

Figure 8A:
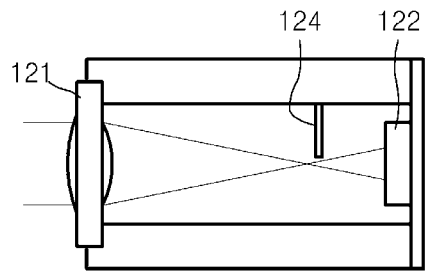
FIGS. 8A, 8B, 9A, 9B, 10A, and 10B illustrate the principle of adjusting a focal point using a knife-edge in the fluorescence detecting optical system of FIG. 6.
Figure 8B:
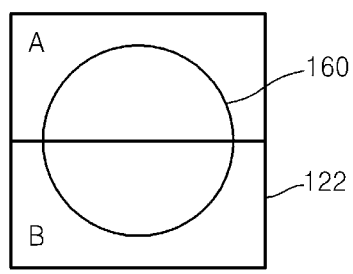

FIGS. 8A, 8B, 9A, 9B, 10A, and 10B illustrate the principle of adjusting a focal point using a knife-edge in the fluorescence detecting optical system 400 of FIG. 6. When the focal point is adjusted using a knife-edge, the focusing lens 121 may be a general convex lens and the divided-type photodetector 122 may be a dual type photodetector having two segments A and B. The knife-edge 124 may be disposed between the focusing lens 121 and the divided-type photodetector 122 so as to block off unfocused light. When excitation light is focused precisely on the chamber 151 of the microfluidic device 150, a beam diameter of light being focused by the focusing lens 121 becomes the smallest at a position of the knife-edge 124 as shown in FIG. 8A. In this case, because no light is blocked by the knife-edge 124, light intensities measured in the first and second segments A and B are equal to each other (A=B) as shown in FIG. 8B.

Figure 9A:
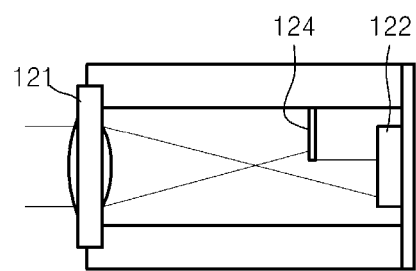
Figure 9B:
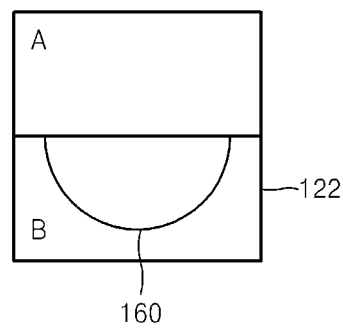
Figure 10A:
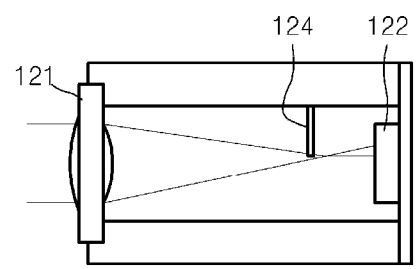
Figure 10B:
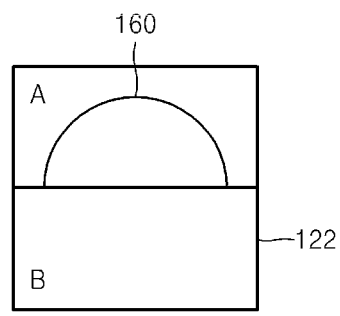

When the objective lens 108 comes too close to the chamber 151 of the microfluidic device 150, a beam diameter of light being focused by the focusing lens 121 becomes the smallest in front of the knife-edge 124 as shown in FIG. 9A. In this case, referring to FIG. 9B, because light directed toward the first segment A is at least partially blocked by the knife-edge 124, light intensity measured in the first segment A is less than light intensity measured in the second segment B (A<B). When the objective lens 108 is too far away from the chamber 151 of the microfluidic device 150, a beam diameter of light being focused by the focusing lens 121 becomes the smallest past the knife-edge 124 as shown in FIG. 10A. In this case, referring to FIG. 10B, because light directed toward the second segment B is at least partially blocked by the knife-edge 124, light intensity measured in the first segment A is greater than light intensity measured in the second segment B (A>B). By using this principle, it is possible to check whether the excitation light is focused precisely on the chamber 151 of the microfluidic device 150.

As described above, even when the microfluidic device 150 is not disposed at the precise position, the fluorescence detecting optical system 400 of FIG. 6 performs an automatic focusing function to automatically focus on the chambers 151 within the microfluidic device 150. Thus, the fluorescence detecting optical system 400 eliminates the need to use an expensive, high-precision, low-vibration drive mechanism for precisely positioning the microfluidic device 150. Although the divided-type photodetector 122 has been described to detect excitation light reflected by the first polarizing beam splitter 105, it may be disposed to detect excitation light reflected by the second polarizing beam splitter 110. The automatic focusing unit 121 through 123 may also be applied to the fluorescence detecting optical systems 100 and 200 described with reference to FIGS. 1 and 4. Because the rest of the construction and operation of the fluorescence detecting optical system 400 are the same as those of the fluorescence detecting optical system 300 described with reference to FIG. 5, a detailed explanation thereof is omitted.

While a fluorescence detecting optical system and a multi-channel fluorescence detection apparatus including the same according to the present invention have been particularly shown in the drawings and described with reference to preferred embodiments thereof in order to aid in the understanding of the present invention, it should be understood that the exemplary embodiments described therein should be considered in a descriptive sense only and not for purposes of limitation. That is, it would be obvious to those of ordinary skill in the art that various changes in form and details may be made therein. Descriptions of features or aspects within each embodiment should typically be considered as available for other similar features or aspects in other embodiments.

What is claimed is:
1. A fluorescence detecting optical system comprising:
a light source unit that emits excitation light having a first polarization component;
an objective lens positioned to focus the excitation light onto a microfluidic device;
a fluorescence detector for detecting fluorescent light generated when a sample within the microfluidic device is excited with the excitation light; and
a light delivery unit that delivers the excitation light emitted by the light source unit to a microfluidic device, and delivers the fluorescent light generated in the microfluidic device to the fluorescence detector,
wherein the light delivery unit is configured to convert excitation light reflected from the microfluidic device to excitation light having a second polarization component perpendicular to the first polarization component and reflect the excitation light having the second polarization component away from an optical path.

2. The system of claim 1, wherein the light delivery unit comprises:
a first beam splitter, disposed between the objective lens and the fluorescence detector, configured to transmit at least a portion of incident light and reflect a remaining portion of incident light;
a second beam splitter, disposed between the first beam splitter and the light source unit, configured to transmit light with the first polarization component and reflect light with the second polarization component;
a first quarter-wave plate disposed between the second beam splitter and the first beam splitter;
a third beam splitter, disposed between the first beam splitter and the fluorescence detector, configured to transmit light with the first polarization component and reflect light with the second polarization component; and
a second quarter-wave plate disposed between the third beam splitter and the first beam splitter.

3. The system of claim 2, wherein the first beam splitter is a half mirror that transmits approximately 50 percent of incident light and reflects the remaining portion of incident light, or a dichroic filter that reflects excitation light and transmits fluorescent light.

4. The system of claim 2, wherein the second beam splitter and the third beam splitter are polarizing beam splitters.

5. The system of claim 2, further comprising an automatic focusing unit that detects excitation light having the second polarization component reflected by the second beam splitter or the third beam splitter, calculates a focus error of the objective lens, and adjusts a focus position of the objective lens.

6. The system of claim 1, wherein the light source unit comprises:
a light source that emits excitation light;
a polarizer that transmits light having the first polarization component and blocks light having the second polarization component perpendicular to the first polarization component; and
a collimating lens that collimates the excitation light into a parallel beam.

7. The system of claim 6, wherein the light source unit further includes an excitation light filter that transmits excitation light in a predetermined wavelength band.

8. The system of claim 1, wherein the fluorescence detector comprises:
a photodetector for detecting fluorescent light emitted from a sample within a microfluidic device; and
a focusing lens positioned to focus the fluorescent light on the photodetector.

9. The system of claim 8, wherein the fluorescence detector further comprising a fluorescent light filter that transmits fluorescent light.

10. The system of claim 1, wherein the light source unit comprises a light source that emits excitation light and a first band pass filter having a transmission band that transmits excitation light in a predetermined wavelength band,
wherein the fluorescence detector comprises a photodetector that detects fluorescent light and a second band pass filter having a transmission band that transmits fluorescent light, and
wherein transmission bands of the first band pass filter and second band pass filter partially overlap.

11. The fluorescence detecting optical system of claim 1, wherein the light source unit emits two excitation light beams having different wavelengths, both light beams having a first polarization component.

12. The system of claim 11, wherein the light delivery unit comprises:
a first beam splitter, disposed between the objective lens and the fluorescence detector, configured to transmit at least a portion of incident light and reflect a remaining portion of incident light;
a second beam splitter, disposed between the first beam splitter and the light source unit, configured to transmit light with the first polarization component and reflect light with the second polarization component;
a first quarter-wave plate disposed between the second beam splitter and the first beam splitter;
a third beam splitter, disposed between the first beam splitter and the fluorescence detector, configured to transmit light with the first polarization component and reflect light with the second polarization component; and
a second quarter-wave plate disposed between the third beam splitter and the first beam splitter.

13. The system of claim 12, wherein the first beam splitter is a half mirror that transmits approximately 50 percent of incident light and reflects the remaining portion of incident light or a dichroic filter that reflects excitation light and transmits fluorescent light.

14. The system of claim 12, further comprising an automatic focusing unit that detects excitation light having the second polarization component reflected by the second beam splitter or the third beam splitter, calculates a focus error of the objective lens, and adjusts a focus position of the objective lens.

15. The system of claim 14, wherein the automatic focusing unit comprises:
a divided-type photodetector with a plurality of photo-detecting segments;
a focusing lens positioned to focus excitation light onto the divided-type photodetector; and
an actuator for adjusting a focus position of the objective lens.

16. The system of claim 15, wherein the focusing lens is an astigmatic lens and the segment type photodetector is a quad type photodetector comprising four photo-detecting segments.

17. The system of claim 15, wherein the automatic focusing unit further includes a knife-edge disposed between the focusing lens and the divided-type photodetector configured to block unfocused light, wherein the divided-type photodetector is a dual type photodetector comprising two photo-detecting segments.

18. The system of claim 11, wherein the light source unit comprises:
a first light source that emits a first excitation light;
a first excitation light filter that passes the first excitation light;
a second light source that emits a second excitation light having a different wavelength than the first excitation light;
a second excitation light filter that passes the second excitation light;

a beam splitter, disposed opposite the first light source and the second light source, configured to reflect or transmit the first excitation light and the second excitation light so that the first excitation light and the second excitation light propagate along the same optical path;

a polarizer that transmits light having the first polarization component and blocks light having the second polarization component perpendicular to the first polarization component; and a collimating lens that collimnates excitation light into a parallel beam.

19. The system of claim 18, wherein each of the first excitation light filter and the second excitation light filter is a dual band pass filter that transmits both the first excitation light and the second excitation light.

20. The system of claim 18, wherein the beam splitter is a half mirror that transmits more than about 95 percent of light incident on a first surface opposite to the first light source and reflects more than about 95 percent of light incident on a second surface opposite to the second light source.

21. The system of claim 20, wherein the light source unit further comprises a monitoring photodetector that measures the intensities of the first excitation light reflected by the beam splitter and the second excitation light transmitted by the beam splitter.

22. The system of claim 11, wherein the fluorescence detector comprises:

a photodetector for detecting fluorescent light emitted from a sample within a microfluidic device; and a focusing lens positioned to focus the fluorescent light on the photodetector.

23. The system of claim 22, wherein the fluorescence detector further comprises a fluorescent light filter that is a dual band pass filter that passes two fluorescent light beams having different wavelengths.

24. A fluorescence detection apparatus comprising:

at least one fluorescence detecting optical system of claim 11; and a transport element that transports the at least one fluorescence detecting optical system.

25. A fluorescence detection apparatus comprising:

at least one fluorescence detecting optical system of claim 1; and a transport element that transports the at least one fluorescence detecting optical system.

26. A fluorescence detecting optical system comprising:

a light source unit that emits excitation light having a first polarization component;

an objective lens;

a fluorescence detector; and a light delivery unit comprising a first beam splitter disposed along an optical path between the objective lens and the fluorescence detector;

a second beam splitter disposed along an optical path between the first beam splitter and the light source unit, wherein the second beam splitter transmits light with the first polarization component and reflects light with a second polarization component perpendicular to the first polarization component;

a first quarter-wave plate disposed along an optical path between the second beam splitter and the first beam splitter;

a third beam splitter disposed along an optical path between the first beam splitter and the fluorescence detector, wherein the second beam splitter transmits light with the first polarization component and reflects light with a second polarization component perpendicular to the first polarization component; and a second quarter-wave plate disposed along an optical path between the third beam splitter and the first beam splitter.

* * * * *